United States Patent
Moncrease (10) Patent No.: US 8,229,758 B2
(45) Date of Patent: Jul. 24, 2012

(54) SYSTEM AND METHOD OF ELECTRONIC MANAGING AND DISPENSING MEDICATION AND PROPHLYACTIC DRUGS IN AN EMERGENCY ENVIRONMENT

(76) Inventor: Anita Verna Moncrease, Detroit, MI (US)

( * ) Notice: Subject to any disclaimer, the term of this patent is extended or adjusted under 35 U.S.C. 154(b) by 277 days.

(21) Appl. No.: 12/252,084

(22) Filed: Oct. 15, 2008

(65) Prior Publication Data

US 2009/0099874 A1  Apr. 16, 2009

Related U.S. Application Data

(60) Provisional application No. 60/980,144, filed on Oct. 15, 2007.

(51) Int. Cl.
*G06Q 10/00* (2006.01)
*G06Q 50/00* (2006.01)
*G08B 1/00* (2006.01)
(52) U.S. Cl. .............................. 705/2; 705/3; 340/539.12
(58) Field of Classification Search .................. 705/2, 3; 340/539.12
See application file for complete search history.

(56) References Cited

U.S. PATENT DOCUMENTS

| | | | |
|---|---|---|---|
| 2002/0059246 A1* | 5/2002 | Rowe | 707/10 |
| 2005/0068175 A1* | 3/2005 | Faulkner et al. | 340/541 |
| 2006/0149416 A1* | 7/2006 | Mohapatra et al. | 700/242 |
| 2006/0206361 A1* | 9/2006 | Logan, Jr. | 705/3 |
| 2007/0263780 A1* | 11/2007 | Lentini | 379/37 |
| 2008/0059236 A1* | 3/2008 | Cartier | 705/3 |
| 2008/0243545 A1* | 10/2008 | D'Ambrosia et al. | 705/2 |

* cited by examiner

*Primary Examiner* — Gerald J. O'Connor
*Assistant Examiner* — Neha Patel
(74) *Attorney, Agent, or Firm* — Sherr & Vaughn, PLLC

(57) ABSTRACT

A system and method for dispensing medication and prophylactic drugs to specific parties at a designated mobile medical workstation during either a municipal, state or national emergency event. The system includes a plurality of mobile medical workstations provided at various geographic locations that are activated only during a municipal, state or national emergency situation. A electronic card is provided to a party for storing personal, medical, biometric and pharmaceutical data and information relating to the party. Upon an identification verification sequence, the medication and prophylactic drugs may be dispensed to the party.

18 Claims, 3 Drawing Sheets

SYSTEM AND METHOD OF ELECTRONIC MANAGING AND DISPENSING MEDICATION AND PROPHLYACTIC DRUGS IN AN EMERGENCY ENVIRONMENT

The present application claims priority under 35 U.S.C. 119 to U.S. Provisional Patent Application No. 60/980,144 (filed on Oct. 15, 2007), which is hereby incorporated by reference in its entirety.

BACKGROUND

During municipal, state or national emergencies, it is essential that emergency workforce such as first responders (i.e., police, fire, emergency medical, public health, etc.) and infrastructure personnel (i.e., water, electricity, gas, sanitation workers) are administered medication and/or prophylactic drugs in an efficient and timely manner in order to maintain civil control and services. Lessons learned through previous emergencies indicate that during instances of an emergency (e.g., the terrorist attacks on the United States on Sep. 11, 2001, wildfires in southern California and Hurricanes Rita and Katrina, etc.), the emergency workforce are forced to make sure their families are safe before ensuring the safety of the public.

During instances of a municipal, statewide or national emergency event, the emergency workforce and/or their families are also at risk. For example, the city of Detroit, Mich. has approximately 7,000 first responders and key infrastructure personnel. The current standards of estimating the number of family members per emergency workforce maybe determined by multiplying the responder and key infrastructure personnel by a factor of 4 or 4.5. The factor of four represents one responder and 3 (or 3.5) family members. Region 2 South (which includes Detroit, Wayne, Macomb, and Oakland Counties) adheres to this standard. This translates into an estimated 28,000 people in Detroit who may require medication and/or prophylactic drugs as soon as an emergency is declared. According to current standards of care, each person may require receipt of sufficient amounts of medication and/or prophylactic drugs for at least three days.

The current system also lack proactive processes for quickly and efficiently identifying and reaching members of the special needs population (i.e., children, elderly, home bound, etc.), proper planning for quickly and efficiently dispensing resources to the special need populations, and/or means for tracking what resources and services are being accessed and utilized in a timely fashion. Therefore, situations such as making crude estimates of the number and type of medication required during an emergency are largely inaccurate. Accordingly, this could leave many of the special needs population untreated.

The current plan involves giving emergency workforce members the number of doses of prophylactic drugs requested during an emergency, which is highly inefficient and prone to abuse. Moreover, the current plan lacks a sufficient response to managing pediatric doses of prophylactic drugs, allergies, and/or special medical needs such as renal failure or the elderly. The reactive nature of the system is also disadvantageous; discovery of an insufficient supply of prophylactic drugs and medication at the time of an emergency can be fatal to many. In the event the emergency lasts in excess of three days, thereby requiring additional medication and/or prophylactic drugs, the current system lacks any protocols for quickly evaluating the response of the prior three days in real time.

SUMMARY

Embodiments relate to a system that gathers accurate personal, biometric, medical data and information of emergency workers such as first responders, infrastructure personnel, and their families prior to a municipal, state or national emergency.

Embodiments relate to a system for rapidly and efficiently dispensing medication and/or prophylactic drugs to emergency workers such as first responders and infrastructure personnel and family members thereof in making sure their families are protected, thereby allowing the emergency workers to perform their professional duties.

Embodiments relate to a system that maintains, prior to a municipal, statewide or national emergency, an accurate database containing personal, biometric, medical data and information emergency workers and their family who require medication and/or prophylactic drugs during the emergency.

Embodiments relate to a system that accurately identifies and distributes dosages of medications and/or prophylactic drugs to meet and surpass the current standard of 800 dosages/day.

Embodiments relate to a system that can serve at least 1,400 individuals at a single site within an eight hour period or at least 4,200 individuals within a twenty-four hour period during a municipal, statewide or national emergency. For example, for seven thousand first responders, infrastructure personnel, and their families (a total of twenty-eight thousand individuals) using the system could receive medications and/or prophylactic drugs within a twenty-four hour period of activating a mobile medical workstation.

Embodiments relate to a system that may include at least one of the following: a storage device for storing one of personal, medical, biometric and pharmaceutical data and information relating to a first party; a request channel for permitting a second party to request the one of personal, medical, biometric and pharmaceutical data and information relating to the first party stored in the storage device; an authorization channel for permitting the first party to authorize transmission of the one of one of personal, medical, biometric and pharmaceutical data and information relating to the first party data and information relating to the first party from the storage device to the second party; and a transmission channel for transmitting at least selected portions of the one of one of personal, medical, biometric and pharmaceutical data and information relating to the first party data and information relating to the first party from the storage device to the second party when the second party has requested the one of one of personal, medical, biometric and pharmaceutical data and information relating to the first party through the request channel and the first party has authorized transmission of the one of one of personal, medical, biometric and pharmaceutical data and information relating to the first party through the authorization channel.

Embodiments relate to a system that may include at least one of the following: a plurality of designated medical work stations that are activated during one of a municipal, state and national emergency; a storage device for storing one of personal, medical, biometric and pharmaceutical data and information relating to a first party; a request channel for permitting a second party located at one of the designated medical work stations to request, during one of a municipal, state and national emergency, the one of personal, medical, biometric and pharmaceutical data and information relating to the first party stored in the storage device; an authorization channel for permitting the first party to authorize transmission of the one of one of personal, medical, biometric and pharmaceutical data and information relating to the first party data and information relating to the first party from the storage device to the second party; and a transmission channel for transmitting at least selected portions of the one of one of personal, medical, biometric and pharmaceutical data and information relating to the first party data and information relating to the first party from the storage device to the second party at one of the designated medical work stations when the second party has requested the one of one of personal, medical, biometric and pharmaceutical data and information relating to the first party through the request channel and the first party has authorized transmission of the one of one of personal, medical, biometric and pharmaceutical data and information relating to the first party through the authorization channel.

Embodiments relate to a method that may include at least one of the following: storing one of personal, medical, biometric and pharmaceutical data and information relating to a first party in a personal electronic storage device having a unique first party identification number; and then authenticating the identity of the first party based on at least one of the unique first party identification number and the biometric data and information; and then transmitting at least portions of the one of personal, medical, biometric and pharmaceutical data and information relating to the first party from the personal electronic storage device to a data and information receiving device during at least one of a municipal, state and national emergency event; and then providing one of medical and pharmaceutical care to the first party based on the transmitted one of personal, medical, biometric and pharmaceutical data and information relating to the first party; and then modifying the one of personal, medical, biometric and pharmaceutical data and information stored in the personal electronic storage device after providing one of medical and pharmaceutical care to the first party.

Embodiments relate to a method that may include at least one of the following: providing a plurality of mobile medical workstations designated at a specified geographic location; and then activating the mobile medical workstations only upon one of a municipal, state and national emergency situation; and then presenting a personal electronic storage device having a unique first party identification number to one of the mobile medical workstations during one of a municipal, state and national emergency, the personal electronic device facilitating the storage of one of personal, medical, biometric and pharmaceutical data and information relating to the first party; and then authenticating at one of the mobile medical workstations and after the presentation of the personal electronic storage device, the identity of the first party based on at least one of the unique first party identification number and the biometric data and information; and then transmitting, at one of the mobile medical workstations, and after authenticating the identity of the first party, at least portions of the one of personal, medical, biometric and pharmaceutical data and information relating to the first party from the personal electronic storage device to a receiving device; and then providing, at one of the mobile medical workstations, one of medical and pharmaceutical care to the first party based on the transmitted one of personal, medical, biometric and pharmaceutical data and information relating to the first party; and then modifying, at one of the mobile medical workstations, the one of personal, medical, biometric and pharmaceutical data and information stored in the personal electronic storage device after providing one of medical and pharmaceutical care to the first party.

DRAWINGS

Example

DESCRIPTION

During a municipal, state or national emergency, it is essential that first responders (e.g., police, National Guard, fire, emergency medical, public health, etc.) and infrastructure personnel (water, electricity, gas, sanitation, etc.) receive medication and/or prophylactic drugs in an efficient and timely manner in order to maintain civil control and services. In accordance with embodiments, electronic information management system 100 may includes at least one of a rapid drug dispensing system (RDDS), a rapid emergency pharmacy system (REPS) and a rapid emergency information system (REIS) to enable rapid and efficient responses to a municipal, state or national emergency.

Figure 1:
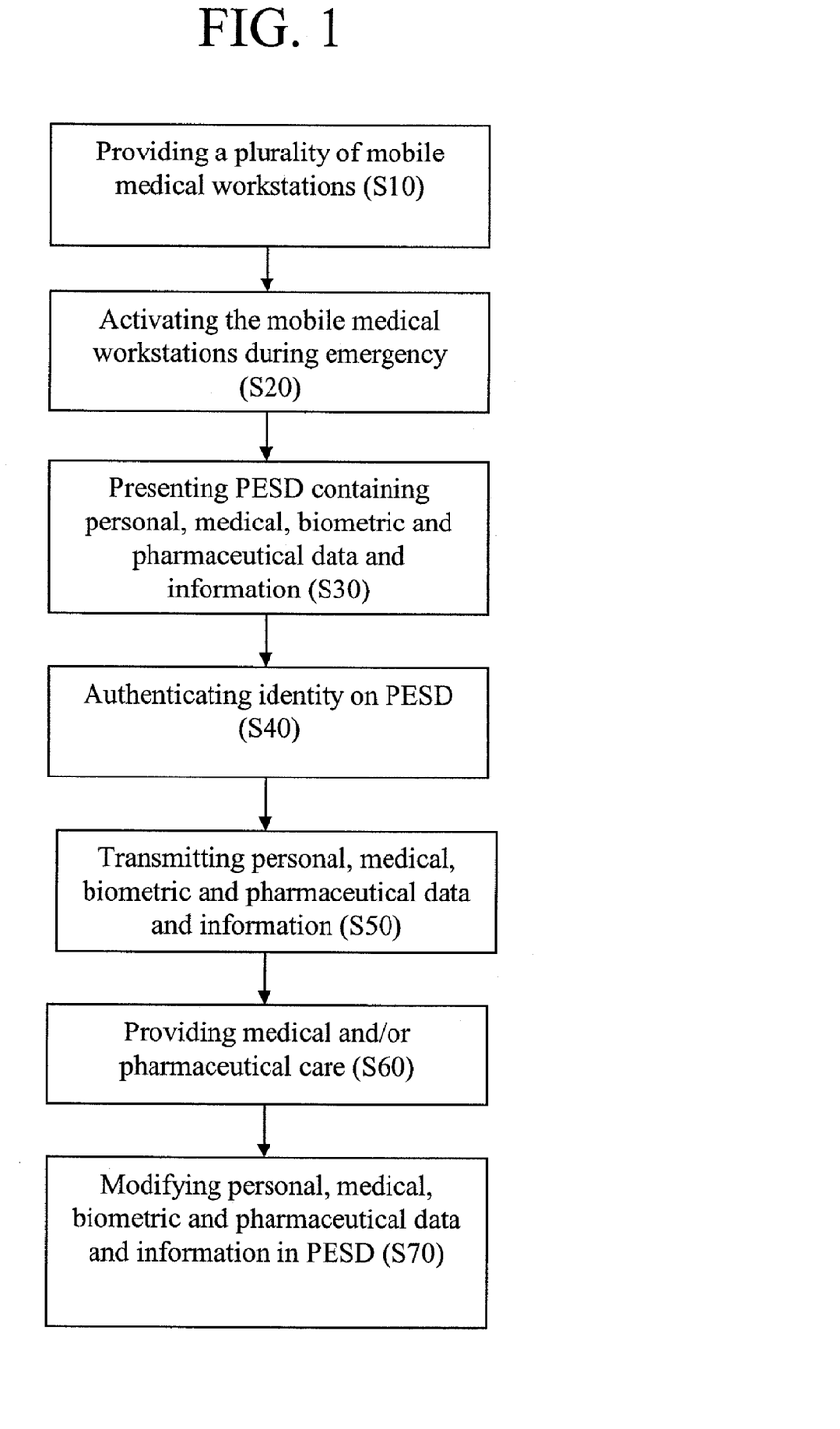
FIGS. 1 through 3 illustrate a method of rapidly managing and dispensing medication and/or prophylactic drugs in accordance with embodiments.

As illustrated in example FIG. 1, a method may include in step S10, providing a plurality of mobile emergency medical workstations designated at a specified geographic location. The number of mobile emergency medical workstations will reflect the overall surrounding population. In step S20, the mobile emergency medical workstations will become fully active only upon the declaration of one of a municipal, state and national emergency. In step S30, a first party who can be an emergency worker, an immediate family member of the emergency worker, or a member of the public at large may present a PESD to a designated one of the mobile medical workstations that is noted on the PESD of the first party. As noted herein, the PESD may contain one of personal, medical, biometric and pharmaceutical data and information relating to the first party.

In step S40, an operator at the designated mobile medical workstation may then authenticate the identity of the first party based on the information provided in the PESD, such as the unique first party identification number and/or the biometric data and information. In step S50, after authenticating the identity of the first party, at least portions of the one of personal, medical, biometric and pharmaceutical data and information relating to the first party is transmitted to the designated mobile emergency medical workstation from the personal electronic storage device to a receiving device such as a card reader or by wireless communication. In step S60, the first party will receive at the designated mobile emergency medical workstation medical and/or pharmaceutical care such as prescription medication and/or prophylactic drugs. Such care, particularly, the type and dosage of the medication and/or prophylactic drugs, etc. may be based on the transmitted personal, medical, biometric and pharmaceutical data and information relating to the first party. Next, in step S70, the personal, medical, biometric and pharmaceutical data and information stored in the PESD is modified to reflect that medication and/or prophylactic drugs have been give and/or received at the designated mobile emergency medical workstation at a particular time and date.

Figure 2:
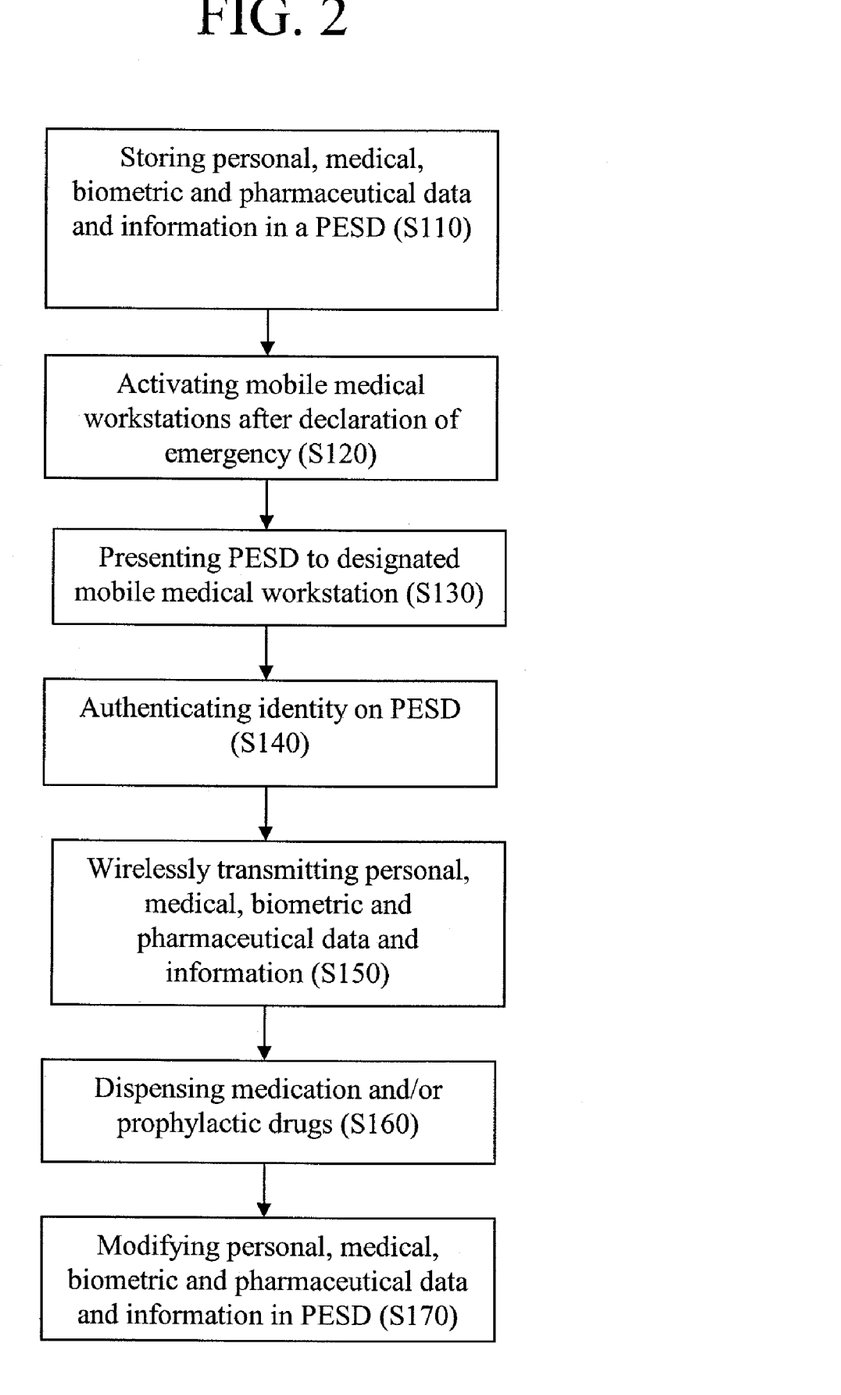

As illustrated in example FIG. 2, in accordance with embodiments, a method may include in step S110, storing one of personal, medical, biometric and pharmaceutical data and information in a PESD. In step S120, a plurality of mobile emergency medical workstations provided at designated geographic locations are activated upon the declaration of a municipal, state and/or national emergency. In step S130, a first party, who can be an emergency worker, an immediate family member of the emergency worker, or a member of the public at large may present a PESD to a designated one of the mobile medical workstations noted on the PESD of the first party. As noted herein, the PESD may contain one of personal, medical, biometric and pharmaceutical data and information relating to the first party.

In step S140, an operator at the designated mobile medical workstation may then authenticate the identity of the first party based on the information provided in the PESD, such as the unique first party identification number and/or the biometric data and information. In step S150, after authenticating the identity of the first party, at least portions of the one of personal, medical, biometric and pharmaceutical data and information relating to the first party is transmitted wirelessly to either the designated mobile emergency medical workstation or a server from the personal electronic storage device. In step S160, the first party will receive at the designated mobile emergency medical workstation medical and/or pharmaceutical care such as prescription medication and/or prophylactic drugs. Such care, particularly, the type and dosage of the medication and/or prophylactic drugs, etc. may be based on the transmitted personal, medical, biometric and pharmaceutical data and information relating to the first party. Next, in step S170, the personal, medical, biometric and pharmaceutical data and information stored in the PESD is modified to reflect that medication and/or prophylactic drugs have been give and/or received at the designated mobile emergency medical workstation at a particular time and date.

Figure 3:
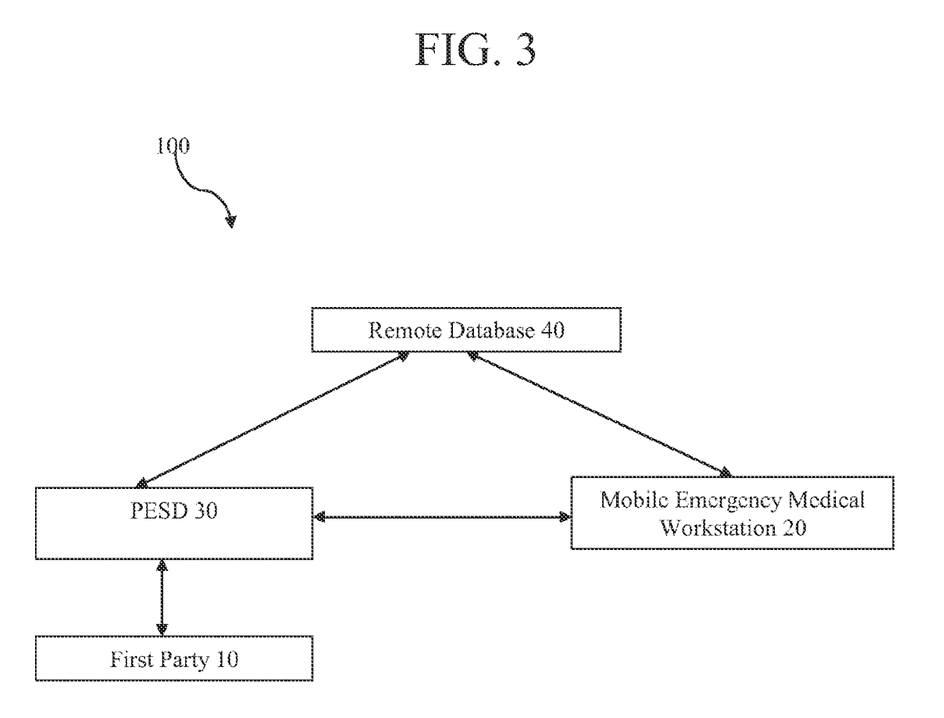

As illustrated in example FIG. 3, in accordance with embodiments, the first party 10, such as an emergency worker (e.g., first responders, infrastructure personnel) and their immediate family members to receive prescribed medication and/or prophylactic drugs at designated mobile emergency medication workstation 20. System 100 develops and maintains in a proactive manner, i.e., prior to the occurrence of a municipal, state or national emergency, accurate personal, medical, biometric and pharmaceutical data and information relating to first party 10. Therefore, first party 10, who may require medication and/or prophylactic drugs during the emergency, to quickly and efficiently receive the same at designated emergency medication workstation 20 during the emergency. Using the stored data and information relating to first party 10, system 100 can generate up-to-date reports in real time.

In accordance with embodiments, system 100 may include personal electronic storage device (PESD) 30 which may take the form of a card embedded with one or more semiconductor devices. PESD 30 can effectively receive and store one of personal, medical, biometric and pharmaceutical data and information relating to first party 10. The personal information and data may be collected in the event the family should be contacted concerning a related adverse event, for example, expired medication and/or trouble with a particular batch of medication.

During a municipal, state, and/or national emergency, first party 10, i.e., a holder of PESD 30, will be enabled to rapidly and efficiently receive at a designated mobile emergency medical workstation 20, after verification of the identity of first party 10, prescribed/un-prescribed medication and/or prophylactic drugs in a rapid, yet efficient manner. PESD 30 may include at an outer surface thereof at least one of photo ID, a unique personal identification number, a readable bar code, and information (e.g., alphanumeric character(s) or a physical address) relating to designated mobile medical workstation 20 so that first party 10 may be informed where they are assigned to obtain the medication and/or prophylactic drugs.

PESD 30 may come in various forms that include several optional features. Each first party 10 may be issued a PESD having a unique number and barcode assigned to it. The PESD can also be used for purposes of photo identification much like a driver's license. Alternatively, PESD 30 may have a smaller size so as to enable it to be securely held on a key chain and usable in conjunction with a photo ID at a designated drug distribution site. Such a design may include a photo ID. For instance, a basic PESD 30 and a "smart" PESD 30 can come in the form of a card sized to be securely held by a key chain. Such a version may only contain barcode identification indicia. In the event of an emergency, the smart PESD 30 maybe used in lieu of the basic PESD 30 provided an additional form of photo ID is provided in order to obtain medications and/or prophylactic drugs at a mobile medical workstation.

The basic PESD 30 may contain at least one of a photo identification, a unique identification number and a corresponding bar code. Data and information relating to first party 10 and/or family member such as the number of adult doses, children doses, special need doses and dosages may be electronically stored not only at PESD 30, but also at remote database 40 having a server. The basic PESD 30 may be a simple bar code PESD 30. In order for the basic PESD 30 to be read, the server must be active. The basic PESD 30 may be used to access the information stored in the server assigned to that specific bar code and unique identification number.

Upon approval, a family member of first party 10 can use the smart PESD 30, and thus, with proper identification can pick up medications and/or prophylactic drugs. Accordingly, the first party 10 may be free to remain at their emergency assignment during the emergency. For example, during an emergency or a declaration of the same, while the emergency worker is on duty, rather than leaving his/her assignment to pick up medications and/or prophylactic drugs, a designated family member may use the smart PESD 30 to pick up the family dosages at the designated mobile medical workstation 20 determined by zip code and the emergency worker can pick up their individual medication and/or prophylactic drugs at mobile medical workstation 20 located near within proximity to their emergency assignment.

The smart PESD 30 may include a barcode containing one of personal, medical, biometric and pharmaceutical data and/or or information of first party 10. However, a server may not be active in order for the data and information stored in the smart PESD 20 to be read. Accordingly, the smart PESD 20 permits the accurate distribution of medication and/or prophylactic drugs in the event servers are inactive. For example, a power line disruption or power outage may render the servers non-operational, thereby rendering the basic PESD 30 ineffective, but not the smart PESD 30. The server may be the vehicle that the smart PESD 30 uses to share information across various mobile medical workstations 20. An onsite scanner located at mobile medical workstation 20 may read the information stored in the bar code of the smart PESD 30, generating paper tickets containing data and information relating to medication and/or prophylactic drugs required by first party 10. Smart PESD 30 will store that data and information until access to the servers is again established.

In accordance with embodiments, an upgraded version of the basic PESD 30 and the smart PESD, 30 referred here as a "maximum" PESD 30, maybe provided. The maximum PESD 30 has enhanced information storage, i.e., is adapted to store great amounts of data and information when compared to the basic and smart PESDs 30. For instance, the maximum PESD 30 may store essential medical information such as family history of diabetes, asthma, etc. Accordingly, in the event first party 10 is either incapacitated and/or cannot verbally articulate such data and information, the data and information can instead be made readily available by accessing the maximum PESD 30. This type of medical information and all other data and information must meet HIPAA guidelines and must be approved by first party 10 before being stored in the maximum PESD. Contact information in the case of an emergency, medication, blood type, etc. can also be stored. Moreover, the maximum PESD 30 may incorporate the features of the basic PESD 30 and the smart PESD 30 while also incorporating a wireless network feature for purposes of verifying identity (as opposed to use of a bar code). Such wireless networking may include global system for mobile communication (GSM), general packet radio services (GPRS), enhanced data GSM environment (EDGE), etc. The maximum PESD 30 could also be used to track activities of first party 10 during an emergency. For example, such activities may include how many times firs party 10 enters and exits a mobile medical workstations 20 during an emergency or the time lapsed when traveling between two or more areas. The maximum PESD 30 may also include a location device such as a global positioning system (GPS) to assist in locating first party 10 during an emergency. For example, the location/tracking feature may be useful in a HAZMAT situation involving a large industrial site where contact is lost with members of the HAZMAT team. This feature may be available in any of the PESD 30 embodiments.

The data and information collected or otherwise stored in PESD 30 will go through a screening process that meets HIPAA (Health Insurance Portability and Accountability Act of 1996) standards, the Office for Civil Rights HIPAA Privacy Rules: Disclosures for Emergency Preparedness—A Decision Tool, and CDC HIPAA Privacy Rule and Public Health Guidance from CDC and the U.S. Department of Health and Human Services. The information and data can be updated in accordance with municipal, state and/or federal guidelines. First party 10 may have access to a secure Homeland Security Webpage to enter updated information that will then undergo a verification process.

Once the data and information is verified, PESD 30 will be automatically updated electronically. The data and information collected and stored in PESD 30 may be updated within twenty-four hours of security verification. For example, such information and data may be posted on a Homeland Security First Responder web page (hosted by a municipality, state and/or federal agency) upon passing a security verification process. Once the data and information in PESD 30 is updated, such data and information will in turn be automatically updated at remote database 40. For example, PESD 30 may include information relating to first party 10, and/or immediate family members thereof. For instance, if the wife of first party 10 gives birth to a child, first party 10 is responsible for updating PESD 30 to include such new information. The newly added information may be updated within forty-eight business hours of approval and/or verification.

As noted above, the personal, medical, biometric and pharmaceutical data and information relating to first party 10 and/or family members thereof will also be electronically stored in remote database 40. Database 40 may be located in a remote primary server and/or a remoter secondary server. Each server should be located in secure and undisclosed locations, and should have a backup emergency generator used soley for the system. Initially, each first party 10 may be given assignments for registering personal, medical, biometric and pharmaceutical data and information relating thereto in order to receive PESD 30. Updating information may occur through a process approved by each municipality, state and/or federal entity. It is preferred that each first party 10 have access (limited or as necessary) to a secure Homeland Security website. Each first party 10 may have twenty-four hour access to the website to update relative personal, medical, biometric and pharmaceutical data and information, which will undergo security verification and approval.

Upon verification of the data and information, the modified data and information will be automatically entered and either a new PESD 30 will be issued to first party 10 or PESD 30 will be updated without replacement. This should occur at least within forty-eight business hours upon verification. In the event of an emergency event, the data and information stored in PESD 30 may only be shared with an Emergency Operation Center (EOC), and thus, will not be available to any third parties such as individuals or municipal, state and/or federal entity without the express permission of the EOC. All information shared will meet HIPPA guidelines.

Use of PESD 30 in the event of an emergency may involve transmitting the data and information stored therein to the database 40 and system 100 will automatically update the data and information in database 40 on the remote server. For example, in the event of an emergency, if PESD 30 is used at any designated mobile medical workstation 20, the data and information maybe automatically transmitted to database 40 within a matter of minutes. PESD 30 cannot be used at another mobile medical workstation 20 until a designated or prescribed amount of dispensed medication has been utilized. The amount of medication dispensed may be a three day supply.

In accordance with embodiments, the REIS is a pre-registration process that permits use of PESD 30 by the public at-large and/or business entities. Accordingly, the overall time to permit information sharing, report generating, and future planning, staging and logistics can be significantly reduced using REIS. Such information can be done in a more accurate manner. The REIS can generate up-to-date reports in real time. Information such as utilization rates, distribution numbers, etc. may be accessible almost instantaneously. Emergency sites that are over-utilized can receive additional medication while those underutilized will receive less or may be reduced.

A plurality if mobile medical workstations 20 are provided at designated geographic areas. A primary mobile medical workstation 20 and a secondary mobile medical workstation 20 may be provided. Each mobile medical workstation 20 may have an emergency generator, wireless remote access and a required backup local area network (LAN), wide area network (WAN) direct connections through a universal serial bus (USB) port, other types of computer readable media, or combinations thereof. Each mobile medical workstation 20 may have a computer terminal designated specifically for use in the event of an emergency to coordinate the activities related to the dispensing of emergency medication and/or prophylactic drugs.

Each mobile medical workstation 20 may have one or a plurality of scanners. The scanners operate on similar principles as those scanners currently in use by municipal parking enforcement personnel to issue parking citations/tickets. A paper copy "ticket" maybe generated for the car and an electronic message is sent to database 40. The scanner/card reader will respond to the reading of the data and information contained in PESD 30, however in the event the card reader is inactive, the unique number assigned to PESD 30 can be entered. The scanners may be modified during an emergency to read PESD 30 or scanners can be purchased for emergency use only. The scanners will transmit the information read from PESD 30 to a computer terminal at mobile medical workstation 20 or at database 40 or computer terminal located at another remote location. Mobile medical workstation 20 will generate a second ticket to give to pharmacy personnel located at mobile medical workstation 20. Mobile medical workstation 20 may also be electrically connected to the remote server at database 40.

An electronic message will be transmitted to the remote server acknowledging that first party 10 is presenting PESD 30 to mobile medical workstation 20. In the case of a basic PESD 30, the server will transmit an electronic signal to the terminal at mobile medical workstation 20 that includes the type of medication and/or prophylactic drugs should be administered and/or delivered to first party 10 based on the information stored in PESD 30. This information will in turn be transmitted to the scanner for generation of a ticket. In the case of a smart or maximum PESD 30, the information may be transmitted directly to the scanner without being routed through the remote server.

For a basic PESD 30, the bar code information may be electrically transmitted from the mobile medical workstation to the central server for translation. The amount, types, and instructions for any medications and/or prophylactic drugs may be transmitted back to mobile medical workstation 20. This data/information may also be shared with other mobile medical workstation 20. Note the server must be operational in order to translate information on barcode. For the smart and maximum PESDs 30, the bar code information may be read at mobile medical workstation 20 and translated. The information may be electrically transmitted to the remote server to be shared with other drug distribution sites. The server does not have to be active for the mobile medical workstation to read the bar code. Once the bar code is read, a ticket or document may be generated at the mobile medical workstation containing the data/information. The entire process at this point should take less than 20 seconds. First party 10 may then be given a ticket by the operator and told to proceed to a pick-up station located at mobile medical workstation 20.

Operator at mobile medical workstation 20 may give a copy of the ticket to pharmacy personnel who then places the medication and/or prophylactic drugs in a container for first party 10 (time varies depending on how pharmacy is organized). When first party 10 arrives at the pick-up station and presents their ticket, the required medications and/or prophylactic drugs (verified by the matching mobile medical workstation ticket) will be issued in addition to verbal and written instructions on how to administer the medications and/or prophylactic drugs (should take less than 20 seconds). Special instructions such as pediatric dosages, allergy alternative medications, etc. may be printed on the ticket and read by the pharmacy personnel to first party 10. If first party 10 does not agree with the data/information on the ticket, they will be directed out of the line into another area to resolve the situation. Directing first party 10 with such issues to another area will allow the line to keep progress so as not to interrupt service to other first parties 10.

The overall time from presenting PESD 30 to receiving medical care may take approximately two to three and one-half minutes/person. For example, it should take approximately twenty seconds to read the PESD, print information, and transmit the information to the mobile medical workstation (three 3/min, 180/hour, or 4320/day), which surpasses the standard industry goal of 800/day. Once the package center located at the mobile medical workstation receives the order for medication, it may take an estimated one to two minutes to package the medication and an additional minute to verify the medication in the package matches that which is printed on the ticket held by the first party.

Hand held scanners will permit greater mobility on the part of the operator, allow for identification verification and confirmation, and initiate the process of packaging the medication and/or prophylactic drugs prior to first party 10 presenting a ticket to the pick-up station. The scanner may read the information on the barcode and the issue a ticket to first party 10 that may include indicia such as the type of medication, the number of dosages, the type of dosages, and how the medication is to be administered. The information contained in the ticket should be verified by first party 10. If the information is incorrect, first party 10 may be directed to another area to correct the information. At the same time the ticket is generated, the information from the scanner may be transmitted to mobile medical workstation 20, the remote central server at database 40, and/or other mobile medical workstations 40.

In accordance with embodiments, servers currently provided at any municipality, state or federal entity can be modified to support system 100. Otherwise, servers can be purchased that will be utilized soley for system 100 during the time of an emergency. It is preferred that system 100 designated servers, i.e., a remote primary server and a remote secondary server. Each server should be located at two separate secure sites and each should have its own secondary or backup generator in the event of a power failure. These servers can also interface with servers used by the municipality, state or federal entity. In order to obtain maximum efficiency of system, it is preferred that a Linux/Unix operating system for open source compatibility be used. This is based on industry standards for productivity and scalability. Other operating systems can be used in the alternative.

System 100 is not limited to use by first responder and/or key infrastructure personnel and may also be used to assist the general public in obtaining medications and/or prophylactic drugs during an emergency. Non-emergency personnel/citizens can receive a version of the PESD in the same manner they receive a readable store PESD at a local drug store or supermarkets. Moreover, during the time of an emergency event, the PESD can be used to assist U.S. postal workers when making their deliveries or when citizens appear at a mobile medical workstation to pick up medication. Families and children in public/private schools and long term facility residence (and their staff) may be issued a version of the PESD. During an emergency, a mobile medical workstation could be assigned and scheduled visit long-term facilities and schools to dispense medication after initially serving first responder and/or key infrastructure personnel. This could ensure rapid and efficient distribution to a majority of citizens. In addition, programs such as Meals On WHEELS® that serve an identifiable elderly population may participate by receiving a version of the PESD prior to an emergency, thereby reaching a larger number of elderly (and their families) not in long term facilities.

Citizens having a PESD may also have the option of presenting it to a mobile medical workstation and receiving their medication, after the first responder are served, or waiting for the postal service to deliver them. The key to success is getting the medications and prophylactic drugs to the population as soon as possible during an emergency. The PESD can assist in enrolling people before the event and rapidly disturbing medication and prophylactic drugs during the event.

Utilization rates, distribution numbers and rates are available almost immediately during the emergency event. If additional cycles of drug distributions are required, drug stockpiles can more accurately be allocated. Therefore, sites that were over utilized can receive additional medications and those that were underutilized can receive less or have its supply reduced in order to compensate. System 100 accurately identifies and distributes dosages of medications and/or prophylactic drugs to meet and surpass the current standard of 800 dosages/day (including special medication requirements such as pediatric illnesses and/or allergies). System 100 accurately identifies how much emergency medication and/or prophylactic drugs have been dispensed, the overall number of first party 10 in receipt of such medication and/or prophylactic drugs, and the time in which such medication and/or prophylactic drugs were dispensed. Accordingly, accurate maintenance of the medication can be ensured.

Although embodiments have been described herein, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A rapid drug dispensing system configured for use only after an official declaration of one of a municipal emergency, a state emergency and a national emergency, the emergency system comprising:
    a plurality of mobile medical workstations each having a computer terminal, each provided at a specified geographic location determined by the federal government, each mobile medical workstation being configured for activation only after the official declaration of one of the municipal emergency, state emergency and national emergency;
    an electronic storage device configured for possession only by one of a first responder, infrastructure personnel, and immediate family members thereof, the storage device also being configured to store at least one of personal data, medical data, biometric data and pharmaceutical data and information relating only to one of the first responder, the infrastructure personnel and the immediate family members thereof;
    a request communication channel configured to permit a second party located at one of the mobile medical workstations, to request only after the official declaration of one of the municipal emergency, state emergency and national emergency, one of the personal data, medical data, biometric data and pharmaceutical data and information stored in the storage device;
    an authorization communication channel configured to permit only one of the first responder, the infrastructure personnel and the immediate family members thereof to authorize transmission of one of the personal data, medical data, biometric data and pharmaceutical data relating to one of the first responder, the infrastructure personnel and the immediate family members thereof data from the storage device to the second party; and
    a transmission communication channel configured to transmit at least selected portions of one of the personal data, medical data, biometric data and pharmaceutical data relating to one of the first responder, the infrastructure personnel and the immediate family members thereof to only the second party at one of the designated mobile medical workstations only upon a request made through the request communication channel by the second party and an authorization of the request made through the authorization communication channel by one of the first responder, the infrastructure personnel and the immediate family members thereof,
    wherein each mobile medical workstation is, equipped with mobile scanners configured to read the information contained in the electronic storage device, and a pharmacy area where prophylactic drugs and medication are dispensed to authorized ones of the first responder, the infrastructure personnel and the immediate family members thereof,
    wherein the mobile scanners are configured to issue a tangible document to authorized ones of the first responder, the infrastructure personnel and the immediate family members thereof, the tangible document having indicia such as the type of medication, the number of dosages, the type of dosages, and how the medication is to be administered.

2. The rapid drug dispensing system of claim 1, further comprising a data/information communication channel configured to permit the second party, after obtaining authorization from at least one of the first responder, the infrastructure personnel and the immediate family members thereof, and at least one of the first responder, the infrastructure personnel and the immediate family members thereof to at least provide one of entry and modification of one of the personal data, medical data, biometric data and pharmaceutical data at one of the mobile medical workstations.

3. The rapid drug dispensing system of claim 2, wherein after the official declaration of one of a municipal emergency, a state emergency and a national emergency, the data/information communication channel permits the second party to modify only one of the personal data, medical data, biometric data and pharmaceutical data that relates to one of the first responder, the infrastructure personnel and the immediate family members thereof which is relevant to the dispensing of prophylactic drugs and medication.

4. The rapid drug dispensing system of claim 1, wherein the transmission communication channel is configured to transmit selected portions of one of the personal data, medical data, biometric data and pharmaceutical data in accordance with instructions provided by one of the first responder, the infrastructure personnel and the immediate family members thereof via the authorization communication channel.

5. The rapid drug dispensing system of claim 1, wherein: the storage device comprises a computer memory associated with an information service provider; and one of the personal data, medical data, biometric data and pharmaceutical data is also stored in a database remote from the mobile medical workstations.

6. The rapid drug dispensing system of claim 5, wherein the request communication channel, the authorization communication channel, and the transmission communication channel comprise a wireless network.

7. The rapid drug dispensing system of claim 6, wherein the wireless network comprises a wireless communication medium by which data and information may travel between the electronic storage device and one of a computing device and a network.

8. The rapid drug dispensing system of claim 1, wherein the authorization communication channel includes a card having an integrated circuit.

9. The rapid drug dispensing system of claim 1, wherein the storage device includes a card having computer readable memory.

10. A method of dispensing one of medicine and prophylactic drugs only after an official declaration of one of a municipal emergency, state emergency and national emergency, the method comprising:

providing a plurality of mobile medical workstations each having a computer terminal and each provided at a specified geographic location determined by the federal government;

providing one of a first responder, infrastructure personnel and immediate family members thereof with an electronic storage device containing and storing one of a personal identification number, personal data, medical data, biometric data and pharmaceutical data relating to one of the first responder, the infrastructure personnel and the immediate family members thereof;

activating the mobile medical workstations only after the official declaration of one of the municipal emergency, state emergency and national emergency;

presenting, after the activating step and only at a respective one of the mobile medical workstations, the electronic storage device;

authenticating, after the presenting step and only at the respective one of the mobile medical workstations, the identity of one of the first responder, the infrastructure personnel and the immediate family members thereof based on at least one of the personal identification number and the biometric data, wherein the authenticating step comprises scanning the electronic storage device with a portable, hand-held scanner configured to read the personal identification number, personal data, medical data, biometric data and pharmaceutical data; and then wirelessly transmitting, using the scanner, the personal identification number, personal data, medical data, biometric data and pharmaceutical data to a server;

transmitting, after the authenticating step and only at the respective one of the mobile medical workstations, at least portions of one of the personal data, medical data, biometric data and pharmaceutical data to a receiving device;

generating, after the transmitting step and only at the respective one of the mobile medical workstations, one of the first responder, the infrastructure personnel and the immediate family members thereof with a tangible document containing data and information relating to at least one of medication and prophylactic drugs required by one of the first responder, the infrastructure personnel and the immediate family members thereof, the tangible document thereby authorizing a receipt of one of medical care and pharmaceutical care to one of the first responder, the infrastructure personnel and the immediate family members thereof;

presenting, after the generating step and only by one of the first responder, the infrastructure personnel and the immediate family members thereof, the tangible document to a medical care professional at one of the mobile medical workstations;

dispensing at one of the mobile medical workstations, and after the presenting step, one of medical care and pharmaceutical care to one of the first responder, the infrastructure personnel and the immediate family members thereof based upon the data and information contained on the tangible document; and then modifying, after the dispensing step and only at the respective one of the mobile medical workstations, one of the personal data, medical data, biometric data and pharmaceutical data in the electronic storage device.

11. The method of claim 10, further comprising, after the modifying step: storing one of the personal data, medical data, biometric data and pharmaceutical data at a site located remote from the respective one of the mobile medical workstations.

12. The method of claim 11, wherein the site includes a server.

13. The method of claim 10, wherein the electronic storage device includes a card having computer readable memory.

14. A drug dispensing system configured for use only after an official declaration of one of a municipal emergency, state emergency and national emergency, the drug dispensing system comprising:

a plurality of mobile medical workstations each having a computer terminal designated at a predetermined geographic location, each one of the mobile medical workstations being operationally activated only after the official declaration of one of the municipal emergency, state emergency and national emergency;

a storage device configured to store one of personal data, medical data, biometric data and pharmaceutical data relating to one of a first responder, an infrastructure personnel and immediate family members thereof;

a first communication channel configured for access by a second party other than one of the first responder, the infrastructure personnel and the immediate family members thereof, only after the official declaration of one of the municipal emergency, state emergency and national emergency, one of the personal data, medical data, biometric data and pharmaceutical data and information stored in the storage device;

a second communication channel in operational communication with the first communication channel, the second communication channel being configured to permit one of the first responder, the infrastructure personnel and the immediate family members thereof to authorize, only after a request has been made on the first communication channel by the second party, transmission of one of the personal data, medical data, biometric data and pharmaceutical data from the storage device to the second party; and a third communication channel in operational communication with at least one of the first communication channel and the second communication channel, the third communication channel being configured to wirelessly transmit, after authorization has been made by one of the first responder, the infrastructure personnel and the immediate family members thereof via the second communication channel, at least selected portions of one of the personal data, medical data, biometric data and pharmaceutical data, wherein each mobile medical workstation is equipped with mobile scanners configured to read information contained in the storage device, and a pharmacy area where prophylactic drugs and medication are dispensed to authorized ones of the first responder, the infrastructure personnel and the immediate family members thereof, wherein the mobile scanners are configured to issue a tangible document to authorized ones of the first responder, the infrastructure personnel and the immediate family members thereof, the tangible document having indicia such as the type of medication, the number of dosages, the type of dosages, and how the medication is to be administered.

15. The drug dispensing system of claim 14, further comprising a fourth communication channel in operational communication with at least one of the first communication channel, the second communication channel and the third communication channel, the fourth communication channel being configured to permit at least entry and modification of one of the personal data, medical data, biometric data and pharmaceutical data.

16. The drug dispensing system of claim 14, wherein:
the storage device comprises a computer memory associated with an information service provider; and
one of the personal data, medical data, biometric data and pharmaceutical data is also stored in a database remote from the mobile medical workstations.

17. The drug dispensing system of claim 14, wherein the first communication channel, the second communication channel, and the third communication channel comprise a wireless network.

18. The drug dispensing system of claim 17, wherein the wireless network comprises a wireless communication medium by which data and information may travel between the electronic storage device and one of a computing device and a network.

* * * * *